United States Patent
Seo

(10) Patent No.: US 12,076,088 B2
(45) Date of Patent: Sep. 3, 2024

(54) VIRTUAL REALITY-BASED PORTABLE NYSTAGMOGRAPHY DEVICE AND DIAGNOSTIC TEST METHOD USING SAME

(71) Applicant: M.I.One Co., Ltd., Gangwon-do (KR)

(72) Inventor: Young Joon Seo, Wonju-si Gangwon-do (KR)

(73) Assignee: M.I.ONE CO., LTD., Gangwon-do (KR)

( * ) Notice: Subject to any disclaimer, the term of this patent is extended or adjusted under 35 U.S.C. 154(b) by 610 days.

(21) Appl. No.: 17/299,195

(22) PCT Filed: Dec. 5, 2018

(86) PCT No.: PCT/KR2018/015293
§ 371 (c)(1),
(2) Date: Jun. 2, 2021

(87) PCT Pub. No.: WO2020/116669
PCT Pub. Date: Jun. 11, 2020

(65) Prior Publication Data
US 2022/0071484 A1   Mar. 10, 2022

(30) Foreign Application Priority Data
Dec. 4, 2018   (KR) .................. 10-2018-0154209

(51) Int. Cl.
*A61B 3/113*   (2006.01)
*A61B 3/00*   (2006.01)
(Continued)

(52) U.S. Cl.
CPC ............ *A61B 3/113* (2013.01); *A61B 3/005* (2013.01); *A61B 3/14* (2013.01); *G02B 30/34* (2020.01);
(Continued)

(58) Field of Classification Search
CPC .......... A61B 3/113; A61B 3/005; A61B 3/14; A61B 5/6803; A61B 3/08; A61B 5/398;
(Continued)

(56) References Cited

U.S. PATENT DOCUMENTS 6,108,634 A * 8/2000 Podnar ................. G16H 40/63
351/200
2016/0363770 A1   12/2016 Kim et al.

FOREIGN PATENT DOCUMENTS

KR   10-2015-0144851 A   12/2015
KR      10-1704442 B1    2/2017
(Continued)

OTHER PUBLICATIONS

International Search Report dated Sep. 3, 2019 for International Patent Application No. PCT/KR2018/015293 (Authorized officer, Unknown), 4 pages with English translation.

*Primary Examiner* — Tuyen Tra
(74) *Attorney, Agent, or Firm* — MH2 TECHNOLOGY LAW GROUP, LLP

(57) ABSTRACT

There is provided a VR-based portable nystagmus test apparatus that provides both a three-dimensional stereoscopic image and a voice to a subject such that efficiency and accuracy of a follow-up examination can be enhanced. The VR-based portable nystagmus test apparatus can enhance the accuracy and efficiency of an examination by inducing the subject to make a correct motion, during the examination on the subject who wears the VR-based portable nystagmus test apparatus.

12 Claims, 6 Drawing Sheets

(51) Int. Cl.
  *A61B 3/14*    (2006.01)
  *G02B 30/34*   (2020.01)
  *G16H 20/30*   (2018.01)
  *H04N 13/239*  (2018.01)
  *H04N 13/296*  (2018.01)
  *H04N 13/332*  (2018.01)
  *H04N 13/398*  (2018.01)

(52) U.S. Cl.
  CPC ........... *G16H 20/30* (2018.01); *H04N 13/239* (2018.05); *H04N 13/296* (2018.05); *H04N 13/332* (2018.05); *H04N 13/398* (2018.05)

(58) Field of Classification Search
  CPC ...... A61B 5/4863; A61B 3/145; G02B 30/34; G16H 20/30; G16H 30/20; G16H 30/40; G16H 40/63; G16H 70/20; H04N 13/239; H04N 13/296; H04N 13/332; H04N 13/398
  See application file for complete search history.

(56) References Cited

FOREIGN PATENT DOCUMENTS

| | | |
|---|---|---|
| KR | 10-1725712 B1 | 4/2017 |
| KR | 10-2017-0136582 A | 12/2017 |
| KR | 10-2018-0074401 A | 7/2018 |
| KR | 10-1880386 B1 | 7/2018 |

* cited by examiner

VIRTUAL REALITY-BASED PORTABLE NYSTAGMOGRAPHY DEVICE AND DIAGNOSTIC TEST METHOD USING SAME

CROSS-REFERENCE TO RELATED APPLICATIONS

This application is a U.S. National Stage application of PCT/KR2018/015293 filed 5 Dec. 2018, which claims priority to Korean Application No. 10-2018-0154209 filed 4 Dec. 2018, the entire disclosures of which are hereby incorporated by reference in their entireties.

TECHNICAL FIELD

The present invention relates to a VR-based portable nystagmus test apparatus and an examination method using the VR-based portable nystagmus test apparatus that provides both a three-dimensional stereoscopic image and a voice to a subject such that efficiency and accuracy of a follow-up examination can be enhanced.

BACKGROUND ART

Nystagmus means 'nystagmus as a vision condition' and is an involuntary and rapid rhythmic eye movement. The nystagmus can be caused by a special condition even in normal circumstances, and this kind of nystagmus is referred to as physiologic nystagmus. However, another type of nystagmus is pathologic nystagmus which is caused by a congenital or acquired lesion of an eyeball, nerves, brain, or the like. A test of the nystagmus is an important diagnostic means in clinical investigation of a patient's organ disorder, and many studies on nystagmogram, nystagmus observation, nystagmography, and the like have been conducted for a long time.

A conventional nystagmus test is conducted by using Electro-Nystagmo-Graphy(ENG), Electro-Oculo-Graphy (EOG), Photo-electro-Nystagmo-Graphy(PENG), Frenzel Goggles, and the like.

Although the ENG and EOG are implemented as a very expensive system, there arise a problem of a possibility of interference in recording of eyeball movement due to a baseline change during measurement of electric potential, a problem of low test repeatability due to complexity of test, and a shortcoming of direct attachment of an electrode to a patient's skin during the test. In addition, the PENG has a problem in that a test has to be conducted in a state where an eyeball is open, and the Frenzel goggles have a problem in that it is not possible to record or store eyeball movement.

In this respect, there is development of a video nystagmus test apparatus that can observe and diagnose a patient's eyeball movement and direction relatively more easily than a conventional apparatus for a nystagmus test. Recently, the video nystagmus test apparatus is developed as a wearable apparatus that is worn on a patient such that portability and usability thereof are enhanced.

However, the existing wearable video nystagmus test apparatus induces movement such as eyeball movement and posture movement of a patient by a simple voice order, in a state where the patient is wearing the video nystagmus test apparatus. Hence, in case of a patient examination using an existing nystagmus test apparatus, when a patient does not make a correct motion, accuracy of the test is remarkably decreased, and thus reliability of the test is lowered.

SUMMARY OF INVENTION

Technical Problem

According to the present invention, there are provided a virtual reality (VR)-based portable nystagmus test apparatus and an examination method using the VR-based portable nystagmus test apparatus that provides both a three-dimensional stereoscopic image and a voice to a subject such that efficiency and accuracy of a follow-up examination can be enhanced.

Solution to Problem

According to an embodiment of the present invention, a VR-based portable nystagmus test apparatus is configured of a main body and a band and is worn on a subject. The VR-based portable nystagmus test apparatus includes: a first display that is provided at an inner side of the main body and outputs a displaying image; an optical/imaging unit that is disposed between the first display and both eyes of the subject to provide the displaying image as a stereoscopic image to the subject and image an eyeball of the subject who gazes at the stereoscopic image once or more times; and a control unit that provides both the stereoscopic image and a voice order to the subject depending on a selected examination item and performs an examination on the subject based on one or more eyeball images captured by the optical/imaging unit.

According to another embodiment of the present invention, in an examination method using a VR-based portable nystagmus test apparatus, a subject wears the VR-based portable nystagmus test apparatus, and an examination is conducted on the subject. The examination method includes: a step of generating a stereoscopic image for examination corresponding to an examination item after the examination item for the subject is selected; a step of conducting an examination corresponding to the examination item by providing a voice order along with the stereoscopic image for examination to the subject; a step of outputting an examination result of the subject depending on the examination; and a step of providing a treatment guide for the subject by using the examination result.

Advantageous Effects of Invention

A VR-based portable nystagmus test apparatus of the present invention provides a stereoscopic image and a voice order to a subject to conduct an examination on the subject and thereby can induce the subject to make a correct motion during the examination, and thus accuracy and efficiency of the examination can be enhanced.

In addition, the VR-based portable nystagmus test apparatus of the present invention provides various stereoscopic images and voice orders to the subject and thereby can be applied to various fields of examination, rehabilitation, and the like of ophthalmology-related fields in addition to a nystagmus test, such that applicability of the VR-based portable nystagmus test apparatus can be enhanced.

DESCRIPTION OF EMBODIMENTS

Figure 1:
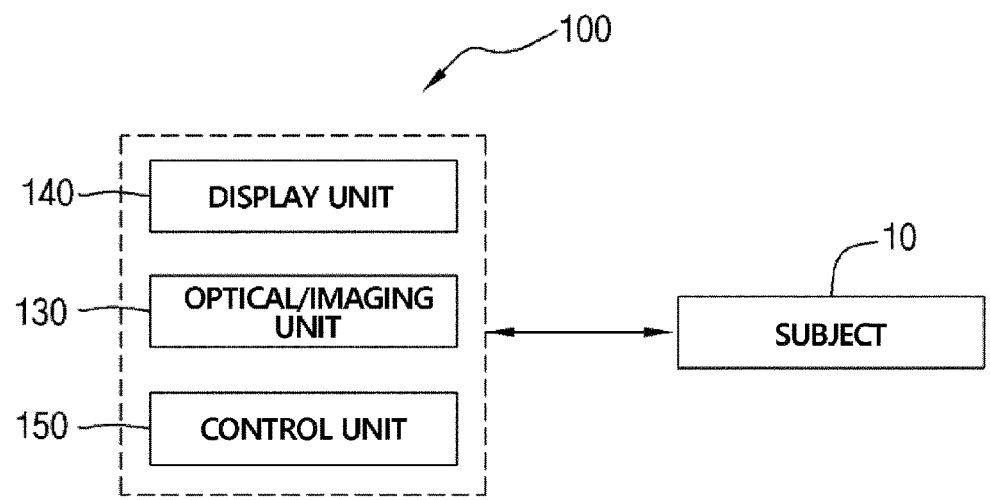
FIG. 1 is a diagram schematically illustrating a configuration of a VR-based portable nystagmus test apparatus according to an embodiment of the present invention.

Hereinafter, configurations and operations of embodiments of the present invention will be described with reference to the accompanying drawings.

It should be noted that like configurational elements will be represented by like reference numerals and signs throughout the drawings as much as possible, even though illustrated on different drawings. In the description of the present invention, when detailed description of a known function or configuration related to the invention is deemed to result in obscuring the gist of the present invention unnecessarily, the detailed description thereof will be omitted. In addition, a case where a certain part "comprises" a certain configurational element means that another configurational element is not excluded but can be further included unless specifically described otherwise.

A term or word, which is used in this specification or claims, is not to be construed in common and dictionary meanings but has to be construed in a meaning and a concept in accordance with a technical idea of the present invention based on the principle that the inventors can appropriately define a concept of a term in order to describe his or her invention in the best way. Consequently, since embodiments described in this specification and configurations illustrated in the drawings are provided only as the preferred embodiments of the present invention and do not represent all of the technical ideas of the present invention, there can be various equivalents and modification examples which can substitute for the embodiments and the configurations of the present invention at the time of this application, and the scope of the present invention is not limited to the embodiments to be described below.

Figure 2A:
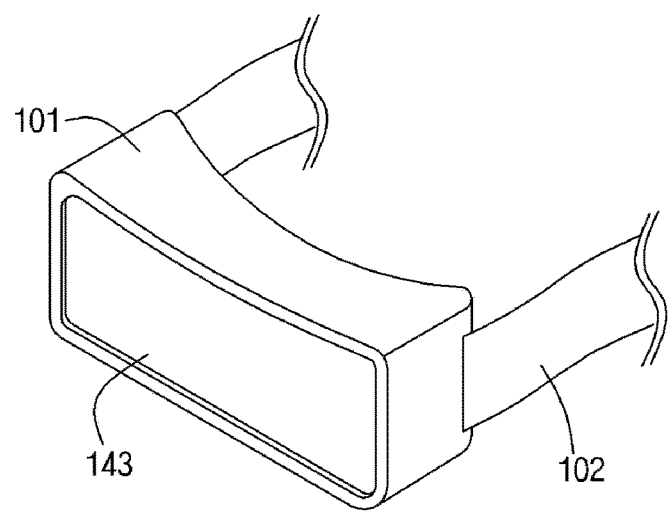
FIG. 2A is a view illustrating a structure of the portable nystagmus test apparatus in FIG. 1.
Figure 2B:
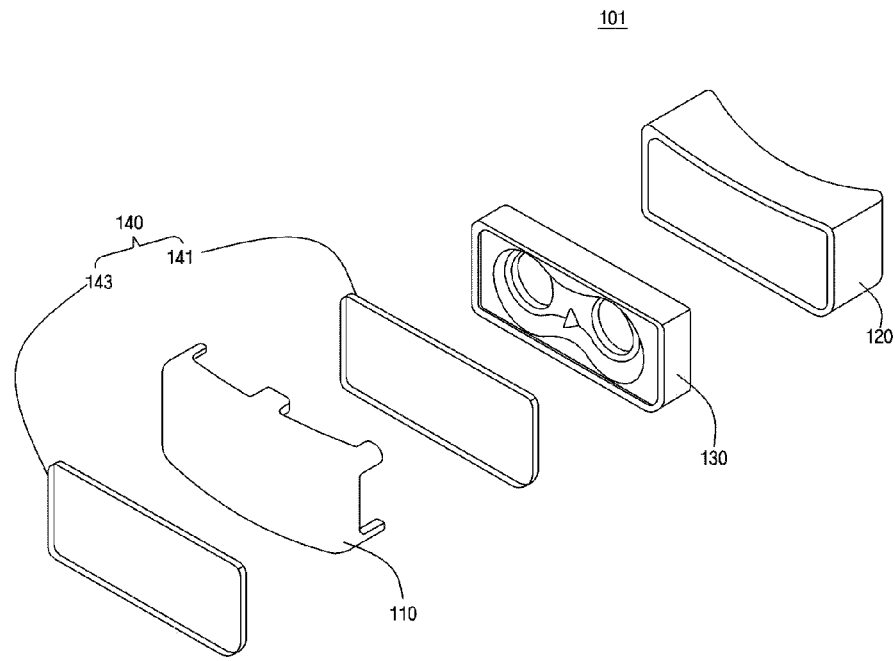
FIG. 2B is an exploded perspective view illustrating a main body in FIG. 2A.
Figure 2C:
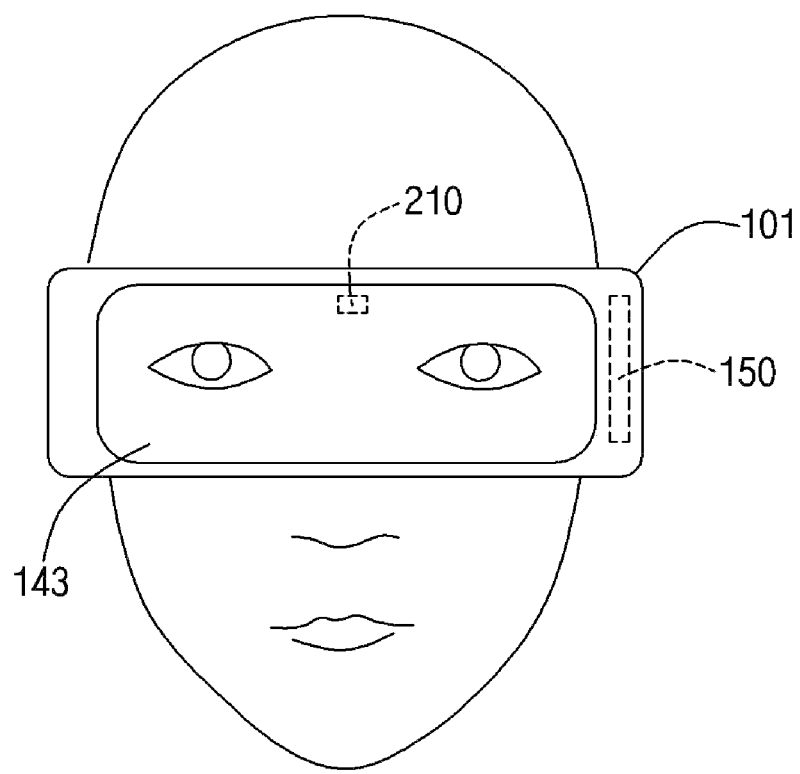
FIG. 2C is a view illustrating a worn state of the portable nystagmus test apparatus on a subject.

FIG. 1 is a diagram schematically illustrating a configuration of a VR-based portable nystagmus test apparatus according to an embodiment of the present invention. FIG. 2A is a view illustrating a structure of the portable nystagmus test apparatus in FIG. 1. FIG. 2B is an exploded perspective view illustrating a main body in FIG. 2A. FIG. 2C is a view illustrating a worn state of the portable nystagmus test apparatus on a subject.

With reference to the drawings, a virtual reality (hereinafter, VR)-based portable nystagmus test apparatus 100 of the embodiment can have a shape of head mounted display (HMD) device which is worn on a user, that is, on a head part of a subject. The VR-based portable nystagmus test apparatus 100 can be configured of a main body 101 and a band 102. The main body 101 can have a goggle shape to come into close contact with the subject's face to block a field of view of the subject from outside. The band 102 can secure the main body 101 to the subject's head.

The main body 101 can be configured of a combination of a front case 110 and a rear case 120. A display unit 140, an optical/imaging unit 130, and a control unit 150 can be disposed inside and outside the main body 101.

The front case 110 and the rear case 120 can have a frame structure which blocks external light. The rear case 120 comes into contact with the subject's face, and thus sealing (not illustrated) made of a flexible and fusible material of silicone, epoxy, polyurethane, or the like can be provided at a contact portion of the rear case. As a result, the rear case 120 can come into close contact with the subject's face.

The display unit 140 can include a first display 141 inside the main body 101 and a second display 143 outside the main body 101. The first display 141 and the second display 143 can be disposed with the front case 110 interposed therebetween.

The first display 141 can display, to the subject, a predetermined image such as a superimposed image of a left eye image and a right eye image corresponding to both eyes of the subject, in response to control of the control unit 150. The second display 143 can display an eyeball image of the subject or a diagnosis result of the subject to the outside in response to control of the control unit 150.

Each of the first display 141 and the second display 143 can be configured of a liquid crystal display (LCD) or an organic light-emitting diode (OLED). In this case, the second display 143 can be configured of a touch display device so as to perform control through a touch from outside.

The optical/imaging unit 130 can be disposed between the first display 141 and the rear case 120 inside the main body 101. The optical/imaging unit 130 can provide a displaying image of the first display 141 as a stereoscopic image to the subject in response to control of the control unit 150. In addition, the optical/imaging unit 130 can image both eyes of the subject who watches an image in response to control of the control unit 150 once or more times, and can output one or more capture images. The optical/imaging unit 130 can be configured to be inserted into the rear case 120 in order to enhance providing accuracy of the stereoscopic image and imaging accuracy of the subject.

The control unit 150 can be disposed inside the main body 101 to control an operation of the display unit 140 and the optical/imaging unit 130. The control unit 150 enables the subject to be provided with both the stereoscopic image and a voice order for examination. In this respect, the subject can conduct a predetermined examination such as a nystagmus test or various ophthalmology-related tests in accordance with the stereoscopic image and the voice order provided in a state of wearing the VR-based portable nystagmus test apparatus 100.

As described above, the VR-based portable nystagmus test apparatus 100 of the embodiment can conduct an examination on the subject by providing the voice order along with the stereoscopic image to the subject in a state where the subject is wearing the apparatus. Consequently, the VR-based portable nystagmus test apparatus can induce the subject to make a correct motion for an examination, compared to a conventional portable nystagmus test apparatus, and thus accuracy and efficiency of the examination can be enhanced. Hereinafter, the VR-based portable nystagmus test apparatus 100 of the present invention will be specifically described with reference to the drawings.

Figure 3:
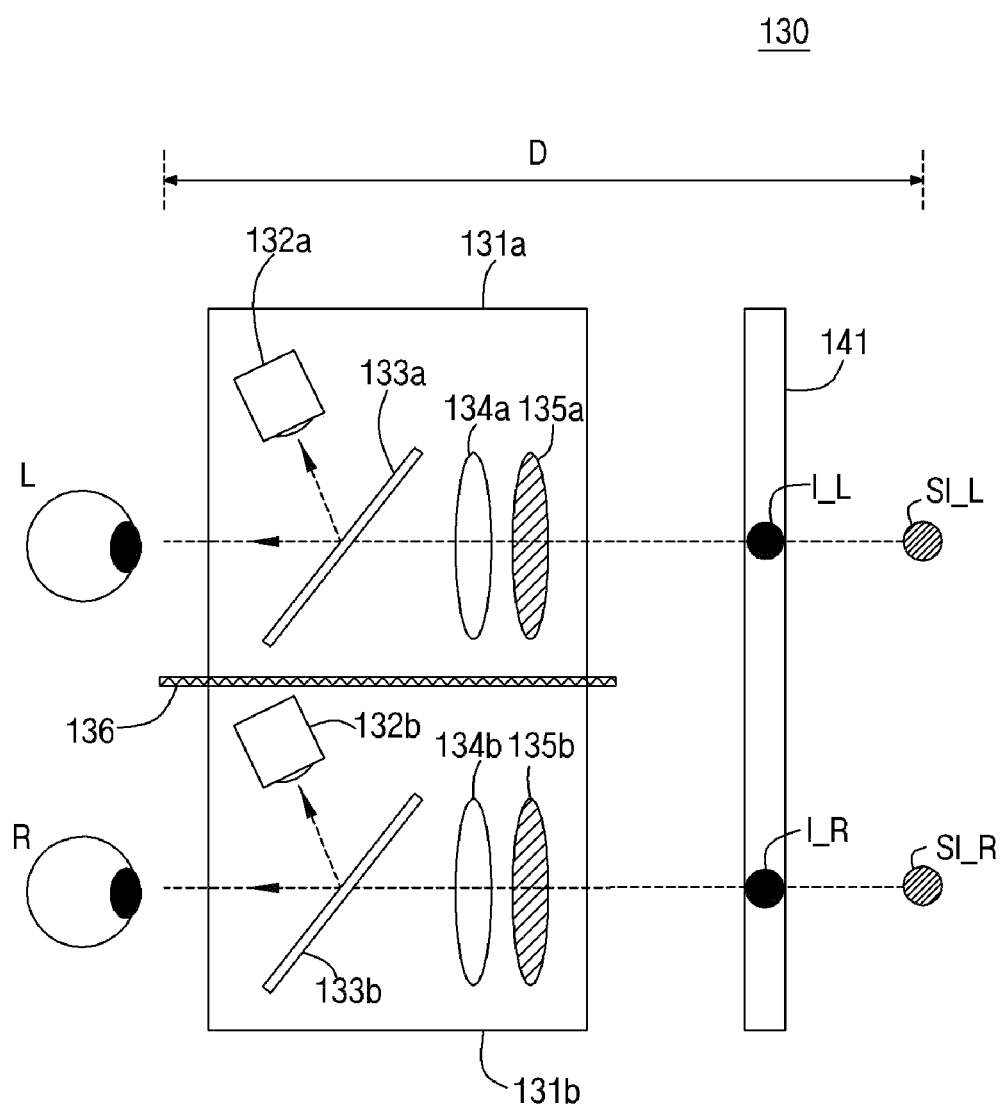
FIG. 3 is a diagram illustrating a configuration of an optical/imaging unit in FIG. 1.

FIG. 3 is a diagram illustrating a configuration of the optical/imaging unit in FIG. 1.

With reference to FIG. 3, the optical/imaging unit 130 of the embodiment can include a first unit 131a and a second unit 131b corresponding to both eyes of the subject and a screen 136 between the two units. The first unit 131a and the second unit 131b can have substantially the same configuration.

The first unit 131a and the second unit 131b can provide displaying images I_L and I_R of the first display 141 as stereoscopic images SI_L and SI_R to the subject, respectively, in response to control of the control unit 150. In other words, the first display 141 displays the two-dimensional displaying images I_L and I_R in which a left eye image I_L and a right eye image I_R are superimposed on each other, and the displaying images I_L and I_R can be provided as three-dimensional stereoscopic images SI_L and SI_R to the subject through the first unit 131a and the second unit 131b, respectively. The stereoscopic images SI_L and SI_R can include a left-eye stereoscopic image SI_L corresponding to the left eye of the subject and a right-eye stereoscopic image SI_R corresponding to the right eye of the subject.

In addition, the first unit 131a and the second unit 131b can image both eyes of the subject who watches the stereoscopic images SI_L and SI_R, respectively, once or more times in response to control of the control unit 150. A captured image can be provided to the control unit 150 and can be used for an examination of the subject.

The first unit 131a and the second unit 131b can include half mirrors 133a and 133b, eyepieces 134a and 134b, polarized lenses 135a and 135b, and cameras 132a and 132b, respectively.

The half mirrors 133a and 133b of the respective units 131a and 131b can be disposed between both eyes of the subject and the first display 141, respectively. The half mirrors 133a and 133b can be disposed to be inclined at an angle of 30 to 50 degrees with respect to the subject or the first display 141.

The half mirrors 133a and 133b can allow both transmission and reflection and thus can be configured of a mirror having a transmittance coefficient to a reflection coefficient of about 50 to 50. The half mirrors 133a and 133b can provide an image incident to a rear surface thereof, that is, a surface corresponding to the first display 141, for example, by transmitting the stereoscopic images SI_L and SI_R, to the subject. In addition, the half mirrors 133a and 133b can reflect both eye images of the subject from front surfaces thereof, that is, surfaces corresponding to both eyes of the subject.

The eyepieces 134a and 134b of the respective units 131a and 131b can be disposed between the half mirrors 133a and 133b and the first display 141, respectively. The eyepieces 134a and 134b can adjust an inter-ocular distance (IOD) and convergence of the stereoscopic images SI_L and SI_R in response to control of the control unit 150. Hence, the eyepieces 134a and 134b can provide the stereoscopic images SI_L and SI_R subjected to adjustment of a sense of three-dimensional effect and a sense of distance to the subject.

The eyepieces 134a and 134b can be configured as a retrofocus type configured of a combination of at least two lenses such as a concave lens and a convex lens. When the control unit 150 adjusts a distance between the two lenses or positions of the eyepieces 134a and 134b, a sense of three-dimensional effect and a sense of distance between the subject and the stereoscopic images SI_L and SI_R can be adjusted on the eyepieces 134a and 134b.

The polarized lenses 135a and 135b of the respective units 131a and 131b can be disposed between the eyepieces 134a and 134b and the first display 141, respectively. However, the polarized lenses 135a and 135b can be disposed between the half mirrors 133a and 133b and the eyepieces 134a and 134b, respectively.

The polarized lenses 135a and 135b can divide and transmit the displaying images I_L and I_R of the first display 141 to correspond to both eyes of the subject, respectively. In other words, the polarized lens 135a and 135b of the first unit 131a can transmit the left eye image I_L corresponding to the left eye of the subject of the displaying images I_L and I_R. The polarized lens 135a and 135b of the second unit 131b can transmit the right eye image I_R corresponding to the right eye of the subject of the displaying images I_L and I_R. The polarized lenses 135a and 135b enables the displaying images I_L and I_R of the first display 141 to be recognized as the stereoscopic images SI_L and SI_R to the subject.

One or more cameras 132a and 132b of the respective units 131a and 131b can be disposed at an upper front side of the half mirrors 133a and 133b, respectively. The cameras 132a and 132b can image once or more times both eyes of the subject which are reflected from front surfaces of the half mirrors 133a and 133b, respectively, in response to control of the control unit 150.

Since the portable nystagmus test apparatus 100 of the present invention is in a state where the external light is blocked from entering the inside of the main body 101, the cameras 132a and 132b of the respective units 131a and 131b can be configured of an infrared camera. In this case, the respective units 131a and 131b can include one or more infrared illuminators (not illustrated) which provide light while the cameras 132a and 132b image both eyes of the subject.

The screen 136 can be disposed between the first unit 131a and the second unit 131b to divide a field of view of both eyes of the subject. The screen 136 enables the left eye image I_L of the displaying images I_L and I_R to be provided through the first unit 131a to the left eye of the subject and enables the right eye image I_R of the displaying images I_L and I_R to be provided through the second unit 131b to the right eye of the subject.

Figure 4:
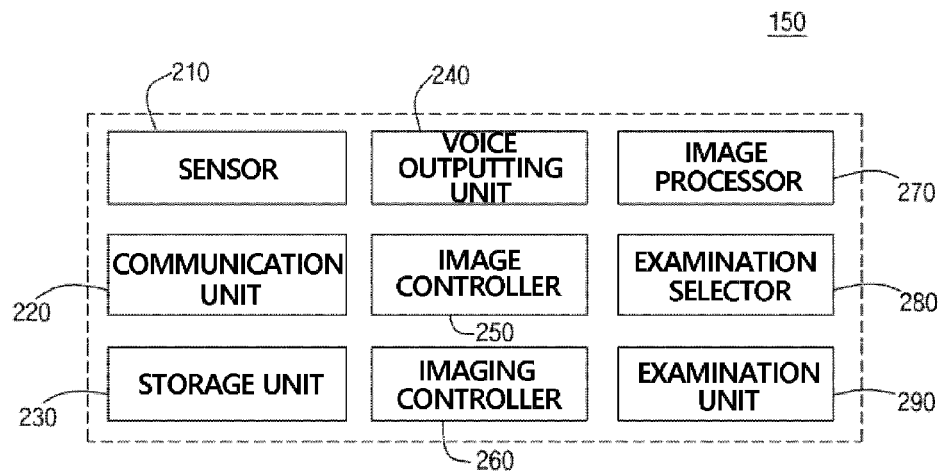
FIG. 4 is a diagram illustrating a configuration of a control unit in FIG. 1.

FIG. 4 is a diagram illustrating a configuration of the control unit in FIG. 1.

With reference to FIG. 4, the control unit 150 of the embodiment can control an operation of the first display 141 and the optical/imaging unit 130 to provide the stereoscopic images SI_L and SI_R to the subject. In addition, the control unit 150 can conduct an examination on the subject by providing a voice order along with the stereoscopic images SI_L and SI_R to the subject.

The control unit 150 can include a sensor 210, a communication unit 220, a storage unit 230, a voice outputting unit 240, an image controller 250, an imaging controller 260, an image processor 270, an examination selector 280, and an examination unit 290.

The sensor 210 can be disposed corresponding to an inner central portion of the main body 101, such as the middle of the forehead of the subject, as illustrated in FIG. 2C. The sensor 210 can detect a state of the portable nystagmus test apparatus 100, such as a tilt or the like of the portable nystagmus test apparatus 100 due to, for example, a posture of the subject. The sensor 210 can transmit a detection result to the examination unit 290 to be described below. The sensor 210 can be configured of at least one of a gravity sensor, a three-axis acceleration sensor, and a three-axis gyro sensor.

The communication unit 220 can be connected to an external device (not illustrated) in a wired or wireless communication way to perform communications between the portable nystagmus test apparatus 100 and the external device. The communication unit 220 can transmit an examination result of the subject which is obtained by the portable nystagmus test apparatus 100 to the external device or can transmit a control signal transmitted from the external device to the control unit 150. When the communication unit 220 is connected to the external device by wire, a predetermined interface (not illustrated) that can be connected to the external device can be formed at an outer surface of the main body 101 of the portable nystagmus test apparatus 100.

The storage unit 230 can store a program for operation control of the control unit 150 or can store the examination result of the subject.

The voice outputting unit 240 can provide a voice order to the subject depending on the examination, when the examination unit 290 conducts the examination on the subject. The voice order can be provided along with the stereoscopic images SI_L and SI_R to the subject.

The image controller 250 can control an operation of the first display 141 and the optical/imaging unit 130 to provide the stereoscopic images SI_L and SI_R to the subject.

The image controller 250 enables the displaying images I_L and I_R corresponding to an examination item selected by the examination selector 280 to be displayed on the first display 141. In this case, the image controller 250 enables the two images, that is, both the left eye image I_L and the right eye image I_R, to be displayed on the first display 141. The image controller 250 can output the left eye image I_L and the right eye image I_R to the first display 141 by encoding the left and right eye images in one way of a right/left way, an upper/down way, a chessboard-shaped way, or a sequential-frame-shaped way.

The image controller 250 can control an operation of the optical/imaging unit 130 to adjust a sense of three-dimensional effect and a sense of distance of the displaying images I_L and I_R of the first display 141. In this respect, the subject can be provided with the stereoscopic images SI_L and SI_R corresponding to the selected examination item through the optical/imaging unit 130. The image controller 250 can adjust an inter-ocular distance, that is, the sense of three-dimensional effect, of the stereoscopic images SI_L and SI_R by adjusting positions of the eyepieces 134*a* and 134*b* by a predetermined distance in a right/left direction such as a right/left direction with respect to both eyes of the subject in the respective units 131*a* and 131*b* of the optical/imaging unit 130. In addition, the image controller 250 can adjust convergence, that is, the sense of distance, of the stereoscopic images SI_L and SI_R by adjusting positions of the eyepieces 134*a* and 134*b* by a predetermined distance in a front/rear direction such as a front/rear direction with respect to both eyes of the subject in the respective units 131*a* and 131*b* of the optical/imaging unit 130.

Hence, as illustrated in FIG. 3, the subject can recognize the displaying images I_L and I_R of the first display 141 as the stereoscopic images SI_L and SI_R displayed behind the first display 141. It is needless to say that the image controller 250 can obviously control the optical/imaging unit 130 to provide the displaying images I_L and I_R displayed three-dimensionally in front of the first display 141 for the subject.

A distance D between the subject and the stereoscopic images SI_L and SI_R subjected to adjustment of the sense of distance by the optical/imaging unit 130 can be changed depending on the selected examination item. For example, when the portable nystagmus test apparatus 100 is used to conduct the nystagmus test on the subject, the image controller 250 can control an operation of the optical/imaging unit 130 to have the distance D of about 1 m between the subject and the stereoscopic images SI_L and SI_R.

The imaging controller 260 enables both eyes of the subject to be imaged at least once by the cameras 132*a* and 132*b* of the optical/imaging unit 130, respectively. The imaging controller 260 can control an imaging operation of the cameras 132*a* and 132*b* in a state where the subject's motion is controlled by the examination unit 290.

The image processor 270 can perform image processing on an image captured by the optical/imaging unit 130, that is, an eyeball image for each of both eyes of the subject. The image processor 270 can transmit a product of image processing to the examination unit 290 such that the product can be used in the examination of the subject. In addition, the image processor 270 can transmit the product of image processing to the second display 143 outside the main body 101 such that the product can be displayed toward the outside. The product of image processing performed by the image processor 270 can contain an outline and a central point extracted from each of the eyeballs and pupils of the subject.

The examination selector 280 can select an examination item of the subject of various examination items. The examination selector 280 can select one of various examinations such as examination items of an eyesight test, vision rehabilitation, and the like in the field of ophthalmology, other than the nystagmus test on the subject. The image controller 250 and the imaging controller 260 can control an operation of the first display 141 and the optical/imaging unit 130 depending on an examination item selected by the examination selector 280.

The examination unit 290 can conduct an examination on the subject depending on the examination item selected by the examination selector 280. The examination unit 290 can induce the subject to have a gaze at the stereoscopic images SI_L and SI_R by providing a voice order to the subject through the voice outputting unit 240 and can control a motion of the subject to conduct the examination depending on the selected examination item.

Figure 5:
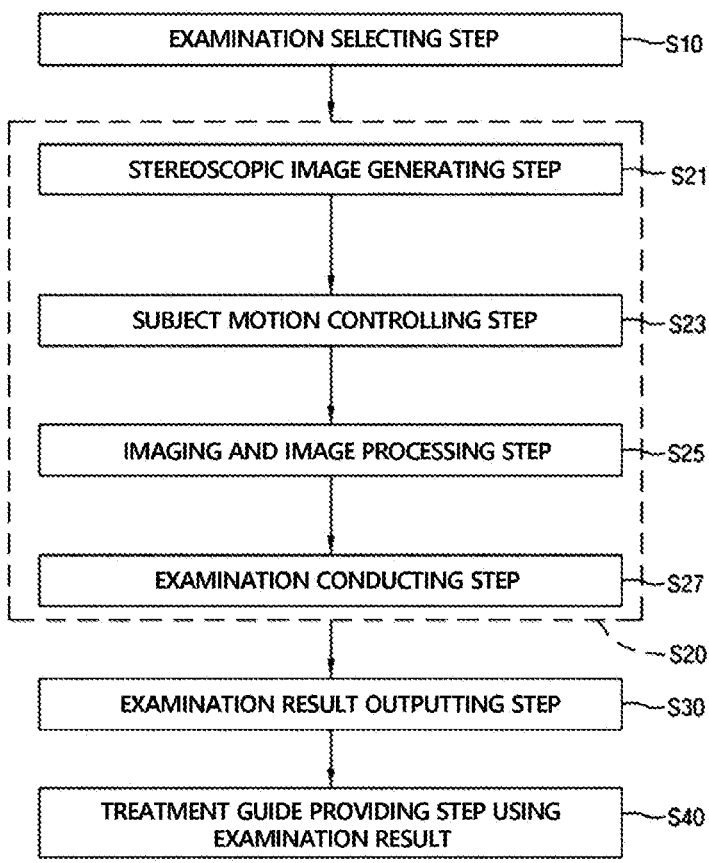
FIG. 5 is a flowchart illustrating an examination method using a VR-based portable nystagmus test apparatus according to another embodiment of the present invention.

FIG. 5 is a flowchart illustrating an examination method using a VR-based portable nystagmus test apparatus according to another embodiment of the present invention. Hereinafter, the examination method of a subject will be described also with reference to FIGS. 3 and 4 described above for convenience of the description.

With reference to FIG. 5, after a subject selects an examination item through the examination selector 280, the subject can wear the portable nystagmus test apparatus 100 (S10).

For example, various examination items can be displayed on the second display 143 of the portable nystagmus test apparatus 100, and the subject can select one of the various examination items by a motion of touching the second display 143. In addition, the subject first wears the portable nystagmus test apparatus 100, and then an external medical staff or the like can select an examination item of the subject.

Next, an examination on the subject depending on the selected examination item can be conducted by providing a voice order along with the stereoscopic images SI_L and SI_R to the subject depending on the selected examination item (S20).

First, the image controller 250 of the control unit 150 can generate the displaying images I_L and I_R corresponding to the selected examination item and enables the displaying images to be displayed on the first display 141. Subsequently, the image controller 250 can control an operation of the optical/imaging unit 130 to provide the displaying images I_L and I_R of the first display 141 as the stereoscopic images SI_L and SI_R for examination to the subject (S21).

The image controller 250 can generate the superimposed displaying images I_L and I_R of the two-dimensional left eye image I_L and right eye image I_R so as to correspond to the selected examination item and can display the superimposed displaying images on the first display 141. The displaying images I_L and I_R can be provided as the three-dimensional stereoscopic images SI_L and SI_R to the subject through the optical/imaging unit 130.

Subsequently, the image controller 250 can generate the stereoscopic images SI_L and SI_R for examination by adjusting the sense of three-dimensional effect and the sense of distance of the stereoscopic images SI_L and SI_R so as to correspond to the selected examination item. The image controller 250 can adjust the inter-ocular distance and the convergence between the subject and the stereoscopic images SI_L and SI_R by moving the eyepieces 134a and 134b of the optical/imaging unit 130 in a predetermined direction, thereby, adjusting the sense of three-dimensional effect and the sense of distance of the stereoscopic images SI_L and SI_R.

When the stereoscopic images SI_L and SI_R for examination are completely generated, the examination unit 290 can provide the voice order depending on the examination to the subject through the voice outputting unit 240 and can control a motion of the subject who gazes at the stereoscopic images SI_L and SI_R (S23).

Subsequently, the imaging controller 260 of the control unit 150 causes the cameras 132a and 132b of the optical/imaging unit 130 to image both eyes of the subject once or more times, and the image processor 270 can perform the image processing on one or more capture images (S25).

Then, the examination unit 290 can conduct the examination on the subject based on an image, that is, an eyeball and pupil image of the subject, subjected to the image processing by the image processor 270 (S27).

The above-described examination steps S21 to S27 of the subject can be repeatedly executed for predetermined times depending on the selected examination item. In addition, the above-described examination steps S21 to S27 of the subject can be partially omitted depending on the selected examination item.

When the examination of the subject by the examination unit 290 is completed, the control unit 150 can output an examination result (S30). The examination result can be displayed toward the outside through the second display 143 of the portable nystagmus test apparatus 100 or can be transmitted to an external device through the communication unit 220.

Subsequently, a treatment guide can be provided to the subject by using the examination result of the subject (S40).

In the step S40, the portable nystagmus test apparatus 100 can provide a stereoscopic image and a voice order for treatment to the subject, based on the treatment guide. In this respect, the subject can perform self-treatment in accordance with the treatment guide of a stereoscopic image and a voice order provided from the portable nystagmus test apparatus 100. Regarding the treatment guide, treatment guides corresponding to various examination results for each examination item can be stored in the storage unit 230 of the control unit 150 of the portable nystagmus test apparatus 100.

Meanwhile, the step S40 of providing the treatment guide can be executed along with the examination step S27.

For example, while the portable nystagmus test apparatus 100 sequentially conducts an examination on the subject depending on the selected examination item, a treatment guide based on a result for each examination step can be provided to the subject in real time. In this case, while the portable nystagmus test apparatus 100 repeatedly conducts the examination on the subject and provides the treatment guide to the subject, the portable nystagmus test apparatus can control a motion of the subject depending on the treatment guide. In addition, the portable nystagmus test apparatus 100 can track a change in examination result due to the self-treatment of the subject in accordance with the treatment guide.

As described above, in the examination method using the portable nystagmus test apparatus 100 of the embodiment, an examination on the subject can be conducted depending on the selected examination item by providing both the stereoscopic image and the voice order to the subject who is wearing the portable nystagmus test apparatus 100, and a result thereof can be outputted. In this respect, the subject can make a correct motion when the examination is conducted in accordance with the stereoscopic image and the voice order which are visually and audibly provided, and thus the accuracy and efficiency of the examination on the subject are enhanced.

In addition, the examination method for the subject by using the portable nystagmus test apparatus 100 of the embodiment can provide the treatment guide based on the examination result to the subject. In this respect, in a state where the subject is wearing the portable nystagmus test apparatus 100, the subject can perform the self-treatment in accordance with the provided treatment guide, and thus the efficiency of the examination and treatment can be enhanced.

Figure 6:
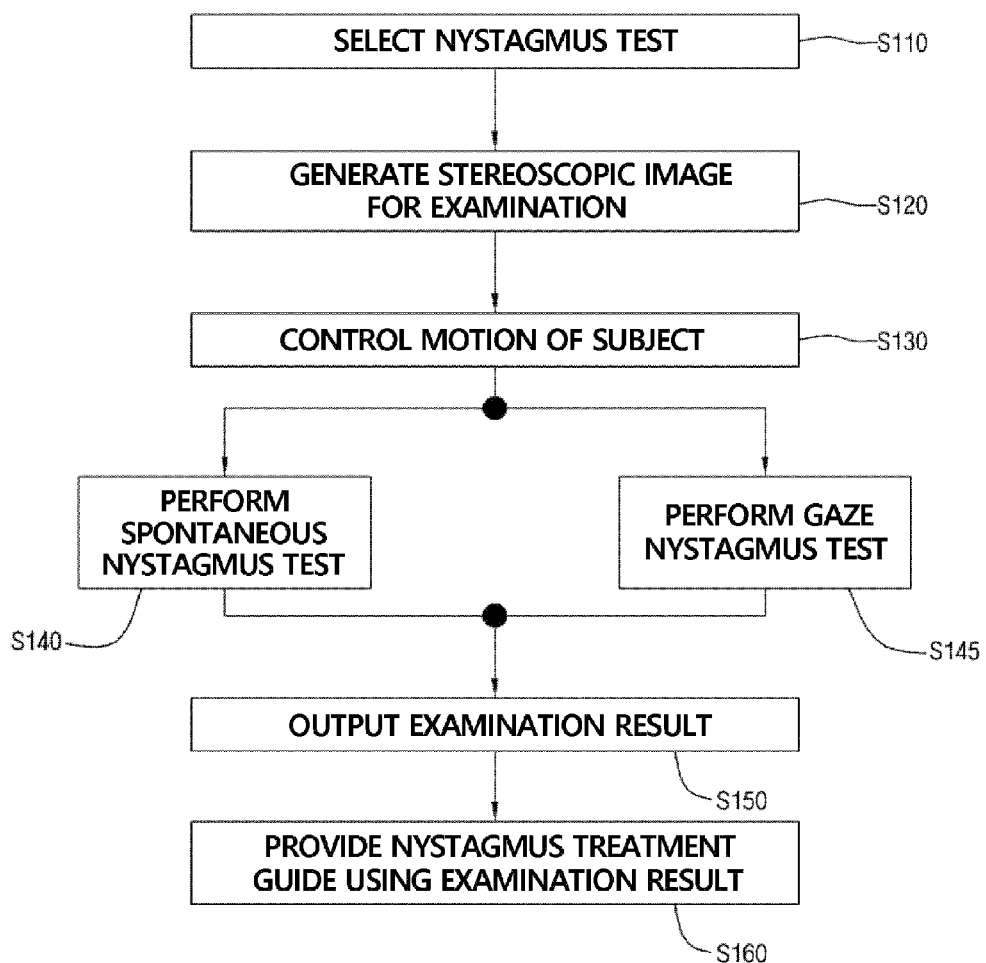
FIG. 6 is a flowchart illustrating a method for conducting a nystagmus test on a subject by using the VR-based portable nystagmus test apparatus of the present invention.

FIG. 6 is a flowchart illustrating a method for conducting a nystagmus test on the subject by using the VR-based portable nystagmus test apparatus of the present invention.

A general nystagmus test can be classified into a test depending on a change in gaze of the subject and a test depending on a change in posture of the subject. Hereinafter, a case where the stereoscopic images SI_L and SI_R and the voice order are provided to the subject using the portable nystagmus test apparatus 100 and the nystagmus test is conducted on the subject from a change in gaze of the subject due to the stereoscopic images and the voice order will be described. However, it is needless to say that the portable nystagmus test apparatus 100 of the present invention can also be used in the nystagmus test depending on a change in posture of the subject.

With reference to FIG. 6, first, the nystagmus test can be selected by the examination selector 280 (S110).

Subsequently, the image controller 250 of the control unit 150 can generate the displaying images I_L and I_R for the nystagmus test and can generate the stereoscopic images SI_L and SI_R for the nystagmus test through adjustment of the sense of three-dimensional effect and the sense of distance of the displaying image (S120).

For example, the image controller 250 can generate the two-dimensional displaying images I_L and I_R for the nystagmus test and can provide the two-dimensional displaying images to the first display 141. Besides, the image controller 250 can adjust the sense of three-dimensional effect and the sense of distance of the stereoscopic images SI_L and SI_R provided to the subject by adjusting positions of the eyepieces 134a and 134b of the optical/imaging unit 130, thereby, providing the stereoscopic images SI_L and SI_R for the nystagmus test to the subject. In this case, since a distance between the subject and the images needs to be set to about 1 m during the nystagmus test, the image controller 250 can adjust the sense of distance between the subject and the stereoscopic images SI_L and SI_R for the nystagmus test through control of the positions of the eyepieces 134a and 134b in a front/rear/right/left direction.

Next, the examination unit 290 can control a motion of the subject based on a sensing result of the sensor 210 (S130) and can conduct a spontaneous nystagmus test on the subject by providing the stereoscopic images SI_L and SI_R and the voice order together to the subject (S140).

First, the examination unit 290 can control the motion of the subject such that the subject gazes at the front by providing the voice order to the subject through the voice outputting unit 240. In this case, the examination unit 290 enables the stereoscopic images SI_L and SI_R to be provided in front of the subject through the image controller 250 and can induce the subject to gaze at the stereoscopic images. Subsequently, the examination unit 290 enables the stereoscopic images SI_L and SI_R to be displayed at the front of the subject, that is, at the middle of both eyes of the subject, and can provide the voice order to induce a gaze of both eyes of the subject at the stereoscopic images SI_L and SI_R. In this case, the examination unit 290 can provide a voice order such that the eyes do not move in a state where the head of the subject is fixed. Besides, the optical/imaging unit 130 can image once or more times each of both eyes of the subject, who gazes at the stereoscopic images SI_L and SI_R, and one or more capture images can be subjected to the image processing to conduct the spontaneous nystagmus test on the subject.

In addition, the examination unit 290 can control the motion of the subject based on the sensing result of the sensor 210 (S130) and can conduct a gaze nystagmus test on the subject by providing the stereoscopic images SI_L and SI_R and the voice order together to the subject (S145).

First, the examination unit 290 can control the motion of the subject such that the subject gazes at the front by providing the voice order to the subject through the voice outputting unit 240. In this case, the examination unit 290 enables the stereoscopic images SI_L and SI_R to be provided to the subject and can induce the subject to gaze at the stereoscopic images. Subsequently, the image controller 250 of the control unit 150 can move the image displayed on the first display 141 in a first direction such as a left direction with respect to each of both eyes of the subject. In this case, the subject can have recognition that the stereoscopic images SI_L and SI_R is moved in the first direction, by the optical/imaging unit 130. The examination unit 290 can provide a voice order to induce a gaze to follow the stereoscopic images SI_L and SI_R which are moved, in a state where the head of the subject is fixed. Subsequently, the optical/imaging unit 130 can image once or more times each of both eyes of the subject as following of the gaze of the subject, who gazes at the stereoscopic images SI_L and SI_R, and one or more capture images can be subjected to the image processing to conduct a leftward gaze nystagmus test on the subject.

Next, the image controller 250 of the control unit 150 can move the image displayed on the first display 141 in a second direction such as a right direction with respect to each of both eyes of the subject. In this case, the subject can have recognition that the stereoscopic images SI_L and SI_R are moved in the second direction, by the optical/imaging unit 130. The examination unit 290 can provide a voice order to induce a gaze to follow the stereoscopic images SI_L and SI_R which are moved, in a state where the head of the subject is fixed. Subsequently, the optical/imaging unit 130 can image once or more times each of both eyes of the subject as following of the gaze of the subject, who gazes at the stereoscopic images SI_L and SI_R, and one or more capture images can be subjected to the image processing to conduct a rightward gaze nystagmus test on the subject.

When both the above-described spontaneous nystagmus test and gaze nystagmus test on the subject are completed, the examination unit 290 can output an examination result (S150). The examination result can be displayed toward the outside through the second display 143 or can be transmitted to an external device through the communication unit 220.

Subsequently, a nystagmus treatment guide can be provided to the subject by using the result of the nystagmus test of the subject such that the self-treatment by the subject can be performed (S160).

In general, dizzy patients often suffer from the nystagmus, and dizziness is mostly caused by otolithiasis. In this respect, in the above-described step S160 of guiding a nystagmus treatment, a guide not for surgery of otolithiasis but for a physical treatment, such as a treatment guide of the Epley Maneuver, the BBQ Maneuver, the reverse Epley Maneuver, the Reverse Semont Maneuver, or the like can be provided. In this case, the portable nystagmus test apparatus 100 can provide a stereoscopic image and a voice order corresponding to the above-described treatment guide to the subject.

In addition, the above-described step S160 of providing the guide for nystagmus treatment can be executed together with the nystagmus test, that is, the spontaneous nystagmus test S140 and the gaze nystagmus test S145.

In other words, when the spontaneous nystagmus test or the gaze nystagmus test is conducted and eyeball movement of the subject is tracked in a state where the subject is wearing the portable nystagmus test apparatus 100, the portable nystagmus test apparatus 100 can provide a treatment guide corresponding to tracked eyeball movement to the subject in real time.

In this case, the portable nystagmus test apparatus 100 can provide a treatment guide including the stereoscopic image and the voice order for the nystagmus treatment to the subject. Besides, the portable nystagmus test apparatus 100 can check whether a motion of the subject is accurately controlled in accordance with the provided nystagmus treatment guide using the optical/imaging unit 130 and the sensor 210. As a result of the check, the portable nystagmus test apparatus can conduct a nystagmus test in the following step and can provide a nystagmus treatment guide.

As described above, in a method of conducting the nystagmus test on the subject by using the portable nystagmus test apparatus 100 of the embodiment, the nystagmus test can be conducted by providing both the stereoscopic image and the voice order, which are visually and audibly provided, to the subject who is wearing the portable nystagmus test apparatus 100, and thereby correct motion of the subject can be controlled in accordance with the nystagmus test. Hence, accuracy of the nystagmus test on the subject can be enhanced.

In addition, in the method of conducting the nystagmus test on the subject according to the other embodiment, a treatment guide is provided as a stereoscopic image and a voice order depending on the nystagmus test to the subject, and thereby the subject can execute a self-treatment for nystagmus in accordance with a treatment guide such that efficiency of the nystagmus test and the treatment thereof can be enhanced.

Meanwhile, the VR-based portable nystagmus test apparatus 100 of the present invention can be used for various ophthalmology-related examinations in addition to the above-described nystagmus test on the subject. Hereinafter, a method for conducting an eye examination on a subject by using the portable nystagmus test apparatus 100 of the present invention will be described with reference to the drawings.

Figure 7:
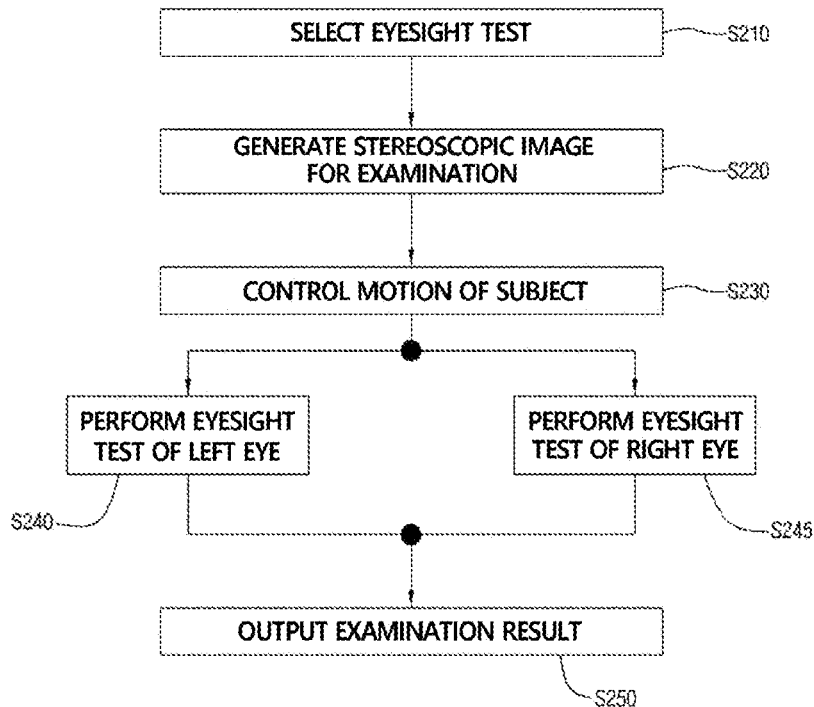
FIG. 7 is a flowchart illustrating a method for conducting an eyesight test on a subject by using the VR-based portable nystagmus test apparatus of the present invention.

FIG. 7 is a flowchart illustrating a method for conducting an eyesight test on a subject by using the VR-based portable nystagmus test apparatus of the present invention.

With reference to FIG. 7, the eyesight test can be selected by the examination selector 280 of the control unit 150 (S210).

Subsequently, the image controller 250 can generate an image for the eyesight test, such as an image of a number or a figure, and can generate the stereoscopic images SI_L and SI_R for the eyesight test through adjustment of the sense of three-dimensional effect and the sense of distance of the image (S220).

The image controller 250 can generate a two-dimensional image for the eyesight test and can provide the two-dimensional image to the first display 141. Subsequently, the operation control of the optical/imaging unit 130 enables the stereoscopic images SI_L and SI_R to be generated by adjusting the sense of three-dimensional effect and the sense of distance of the image displayed on the first display 141. Here, since a distance between the subject and an eyesight test chart needs to be set to 4 m to 5 m in the general eyesight test, the image controller 250 can adjust the sense of distance between the subject and the stereoscopic images SI_L and SI_R for the eyesight test through movement control of the eyepieces 134*a* and 134*b* in a front/rear/right/left direction.

Next, the examination unit 290 can control a motion of the subject based on a sensing result of the sensor 210 (S230). Subsequently, the eyesight test for the left eye can be conducted on the subject by providing both a voice order and the stereoscopic images SI_L and SI_R for the eyesight test corresponding to the left eye of the subject (S240).

Subsequently, the examination unit 290 enables the stereoscopic images SI_L and SI_R for the eyesight test to be outputted to correspond the left eye of the subject and can detect that the subject outputs a feedback such as a voice by recognizing the stereoscopic images SI_L and SI_R for the eyesight test. In this respect, the portable nystagmus test apparatus 100 of the embodiment can further include a microphone (not illustrated) that can collect a voice of the subject. The examination unit 290 can conduct the eyesight test for the left eye on the subject based on a feedback voice of the subject. In this case, no image can be displayed in a right region of the first display 141 by control of the image controller 250 such that a region corresponding to the right eye of the subject comes into a dark state.

In addition, the examination unit 290 can control a motion of the subject based on a sensing result of the sensor 210 (S230). Subsequently, the eyesight test for the right eye can be conducted on the subject by providing both a voice order and the stereoscopic images SI_L and SI_R for the eyesight test corresponding to the right eye of the subject (S245). In this case, no image can be displayed in a left region of the first display 141 by control of the image controller 250 such that a region corresponding to the left eye of the subject comes into a dark state.

When both the above-described eyesight tests for the right and left eyes on the subject are completed, the examination unit 290 can output an examination result (S250). The examination result can be displayed toward the outside through the second display 143 or can be transmitted to an external device through the communication unit 220.

In addition, the VR-based portable nystagmus test apparatus 100 of the present invention can also be used for rehabilitation training of the subject in addition to the above-described nystagmus test and the eyesight test. Hereinafter, a method for performing vision rehabilitation on a subject by using the portable nystagmus test apparatus 100 of the present invention will be described with reference to the drawings.

Figure 8:
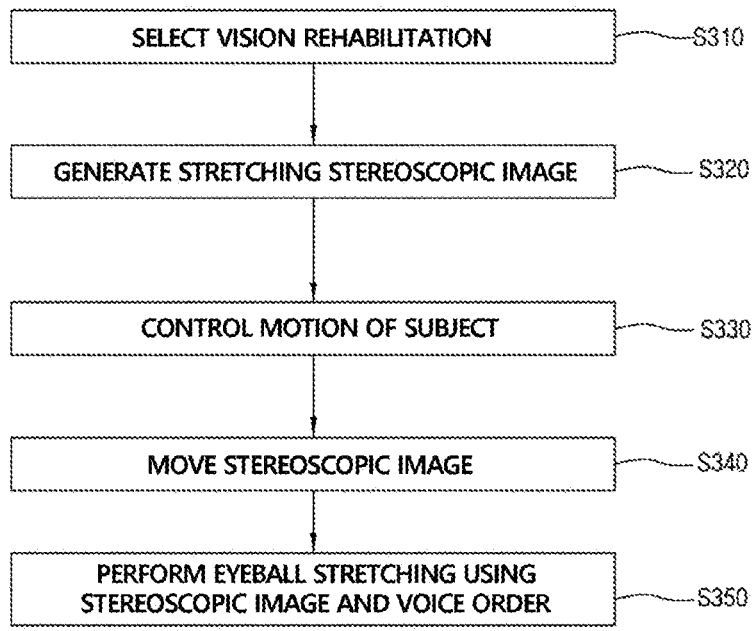
FIG. 8 is a flowchart illustrating a method for performing vision rehabilitation on a subject by using the VR-based portable nystagmus test apparatus of the present invention.

FIG. 8 is a flowchart illustrating a method for performing the vision rehabilitation on the subject by using the VR-based portable nystagmus test apparatus of the present invention.

With reference to FIG. 8, the vision rehabilitation can be selected by the examination selector 280 of the control unit 150 (S310).

Subsequently, the image controller 250 can generate an image for the vision rehabilitation, such as an eyeball stretching image of the subject, and can generate the stereoscopic images SI_L and SI_R for the vision rehabilitation through adjustment of the sense of three-dimensional effect and the sense of distance of the image (S320). Subsequently, the image controller 250 can control a two-dimensional stretching image and can generate stretching stereoscopic images SI_L and SI_R from the two-dimensional stretching image by controlling an operation of the optical/imaging unit 130.

Next, the examination unit 290 can control a motion of the subject depending on a sensing result of the sensor 210 (S330), and the stretching stereoscopic images SI_L and SI_R can be moved in a predetermined direction by the image controller 250 (S340).

Besides, an eyeball movement of the subject can be stretched by inducing the subject to make the eyeball movement follow the moving stretching stereoscopic images SI_L and SI_R in accordance with the voice order (S350). The eyeball stretching of the subject can be repeatedly performed several times, and the vision rehabilitation of the subject can be performed through the eyeball stretching.

As described above, the VR-based portable nystagmus test apparatus 100 of the present invention can conduct an examination on the subject by providing both the stereoscopic image and the voice order to the subject. In this respect, the VR-based portable nystagmus test apparatus 100 of the present invention can induce a correct motion of the subject during conduction of the examination on the subject, and thus the accuracy and efficiency of the examination can be enhanced.

In addition, the VR-based portable nystagmus test apparatus 100 of the present invention provides the stereoscopic images and the voice order for various examinations to the subject and thereby can be used in the examinations and rehabilitation of various ophthalmology-related fields in addition to the nystagmus test of the subject, and thus applicability of the portable nystagmus test apparatus 100 can be enhanced.

INDUSTRIAL APPLICABILITY

The present invention relates to a VR-based portable nystagmus test apparatus and an examination method for conducting various examinations on the subject by using the VR-based portable nystagmus test apparatus which can correctly control a motion of a subject during an examination by providing a stereoscopic image and a voice order to the subject and thus can be serviceably used in development of an HMD device-shaped portable nystagmus test apparatus and in application thereof to various examinations.

The invention claimed is:

1. A VR-based portable nystagmus test apparatus that is configured of a main body and a band to be worn on a subject, the VR-based portable nystagmus test apparatus comprising:
a first display that is provided at an inner side of the main body and outputs a displaying image;
an optical/imaging unit that is disposed between the first display and both eyes of the subject to provide the displaying image as a stereoscopic image to the subject and images an eyeball of the subject who gazes at the stereoscopic image, once or more times; and
a control unit that provides both the stereoscopic image and a voice order to the subject depending on a selected examination item and performs an examination on the subject based on one or more eyeball images captured by the optical/imaging unit,
wherein the optical/imaging unit includes:
a first unit that provides the stereoscopic image to a left eye of the subject and images the left eye of the subject;
a second unit that provides the stereoscopic image to a right eye of the subject and images the right eye of the subject; and
a screen that is disposed between the first unit and the second unit to divide a field of view of the subject, and
wherein the control unit controls each of the first unit and the second unit to adjust an inter-ocular distance and convergence between the subject and the stereoscopic image,
wherein each of the first unit and the second unit includes:
a half mirror that transmits the stereoscopic image incident to a rear surface of the half mirror to provide the stereoscopic image to the subject and reflects both eyes of the subject by a front surface of the half mirror;
one or more cameras that image a reflected image from the half mirror;
an eyepiece which is disposed between the half mirror and the first display and of which a position is controlled by the control unit such that an inter-ocular distance and convergence of the stereoscopic image is adjusted; and
a polarized lens that is disposed between the eyepiece and the first display, separates the displaying image into a left eye image and a right eye image to correspond to both eyes of the subject, and provides the corresponding right or left eye image as the stereoscopic image to the eyepiece.

2. The VR-based portable nystagmus test apparatus according to claim 1,
wherein the control unit includes:
an image controller that outputs the displaying image to the first display to correspond to the selected examination item and controls an operation of the optical/imaging unit to adjust convergence of the stereoscopic image;
an imaging controller that controls an imaging operation of the optical/imaging unit;
an imaging processor that performs image processing on the one or more eyeball images of the optical/imaging unit; and
an examination unit that performs an examination on the subject, based on a processing result of the image processor, to correspond to the selected examination item.

3. The VR-based portable nystagmus test apparatus according to claim 2,
wherein the image controller has functions of
outputting the displaying image as a superimposed image of a left eye image and a right eye image which correspond to both eyes of the subject, and
displaying the stereoscopic image behind the first display by controlling convergence of the stereoscopic image through control of a lens position of the optical/imaging unit.

4. The VR-based portable nystagmus test apparatus according to claim 3,
wherein the image controller controls to adjust a position of the lens of the optical/imaging unit at least in one direction of front/rear/right/left directions with respect to each of both eyes of the subject.

5. The VR-based portable nystagmus test apparatus according to claim 1, further comprising:
a second display that is disposed at an outer surface of the main body and displays both eye images and a diagnosis result of the subject, which are obtained by the control unit, to an outside.

6. An examination method using a VR-based portable nystagmus test apparatus that is worn on a subject, the examination method comprising:
a step of generating a stereoscopic image for examination corresponding to an examination item after the examination item for the subject is selected;
a step of conducting an examination corresponding to the examination item by providing a voice order along with the stereoscopic image for examination to the subject;
a step of outputting an examination result of the subject depending on the examination; and
a step of providing a treatment guide for the subject by using the examination result,
wherein, when a nystagmus test on the subject is selected as the examination item, the step of conducting the examination includes:
a step of generating a stereoscopic image for the nystagmus test;
a step of conducting a spontaneous nystagmus test and a gaze nystagmus test for the subject by providing a voice order along with the stereoscopic image for the nystagmus test to the subject; and
a step of providing a nystagmus treatment guide based on a test result to the subject,
wherein the step of conducting the spontaneous nystagmus test includes a step of providing a voice order to induce a gaze toward the stereoscopic image for the nystagmus test to subject, and
wherein the step of conducting the gaze nystagmus test includes:
a step of moving the stereoscopic image for the nystagmus test in both first and second directions; and
a step of providing a voice order to induce a gaze to follow the stereoscopic image for the nystagmus test which is moved, to the subject.

7. The examination method according to claim 6,
wherein the step of generating the stereoscopic image for examination includes:

a step of generating the displaying image as a superimposed image of a left eye image and a right eye image which correspond to both eyes of the subject, based on the examination item;

a step of providing the displaying image as the stereoscopic image to the subject through an optical/imaging unit; and a step of providing, to the subject, the stereoscopic image for examination subjected to adjustment of an interocular distance and convergence between the subject and the stereoscopic image by controlling the optical/imaging unit.

8. The examination method according to claim 6, wherein the step of conducting the examination corresponding to the examination item includes:

a step of outputting one or more capture images by imaging each of both eyes of the subject through the optical/imaging unit, while controlling a motion of the subject by providing the stereoscopic image for examination and the voice order to the subject;

a step of performing image processing and outputting the one or more capture images; and a step of conducting an examination on the subject to correspond to the selected examination item, based on an image-processed image.

9. The examination method according to claim 6, wherein the stereoscopic image for the nystagmus test is generated by controlling the optical/imaging unit to adjust a distance between the subject and the stereoscopic image for the nystagmus test to about 1 m.

10. The examination method according to claim 6, wherein, in the step of providing the nystagmus treatment guide, the subject is provided in real time with the nystagmus treatment guide corresponding to eyeball movement of the subject which is tracked by conducting the spontaneous nystagmus test and the gaze nystagmus test.

11. The examination method according to claim 6, wherein, when an eyesight test on the subject is selected as the examination item, the step of conducting the examination includes:

a step of generating a stereoscopic image for the eyesight test; and a step of conducting the eyesight test for each of the right and left eyes of the subject by providing a voice order along with the stereoscopic image for the eyesight test to the subject; and wherein the stereoscopic image for the eyesight test is generated by controlling the optical/imaging unit to adjust a distance between the subject and the stereoscopic image for the eyesight test to 4 to 5 m.

12. The examination method according to claim 6, wherein, when vision rehabilitation for the subject is selected as the examination item, the step of conducting the examination includes:

a step of generating an eyeball stretching stereoscopic image; and a step of stretching eyeball movement of the subject by providing a voice order to induce the subject to follow the eyeball stretching stereoscopic image which is moved, while moving the eyeball stretching stereoscopic image, and wherein the step of stretching the eyeball movement of the subject is repeatedly performed.

* * * * *